United States Patent [19]

Sarama et al.

[11] Patent Number: 5,426,248

[45] Date of Patent: Jun. 20, 1995

[54] STABLE VITAMIN A

[75] Inventors: Robert J. Sarama, Loveland, Ohio; Michael R. Sevenants, Newport, Ky.; Robert A. Sanders, Fairfield, Ohio

[73] Assignee: The Procter & Gamble Company, Cincinnati, Ohio

[21] Appl. No.: 285,242

[22] Filed: Aug. 3, 1994

[51] Int. Cl.$^6$ ............................................. C07C 35/18
[52] U.S. Cl. ................................. 568/824; 568/822; 568/8
[58] Field of Search ............... 568/824, 823, 825, 822, 568/862

[56] References Cited

U.S. PATENT DOCUMENTS

| | | | |
|---|---|---|---|
| 2,777,797 | 6/1952 | Hochberg et al. | 424/14 |
| 2,828,206 | 3/1958 | Rosenberg | 99/2 |
| 3,067,104 | 12/1962 | Hochberg et al. | 167/81 |
| 3,067,105 | 12/1962 | Ratfish et al. | 167/81 |
| 3,949,006 | 7/1976 | Oroshnik | 568/824 |
| 4,825,006 | 4/1989 | Otera et al. | 568/824 |
| 4,906,795 | 3/1990 | Grosselin et al. | 568/824 |
| 5,358,972 | 10/1994 | Buck et al. | 568/824 |

FOREIGN PATENT DOCUMENTS

| | | | |
|---|---|---|---|
| WO92/10941 | 7/1992 | European Pat. Off. | A23D 9/00 |
| 887813 | 1/1962 | United Kingdom | 5/2 |

OTHER PUBLICATIONS

Vitamins and Amino Acids, B. Borenstein, CRC Handbook of Food Additives, 3rd ed., Chapter 3 pp. 112–115, 124–126, 129–136, CRC Press, Inc. (1980).
Food Additives Handbook, R. J. Lewis, Sr., p. 375, Van Nostrand Reinhold (1989).
Fat-Soluble Vitamins, Their Biochemistry and Applications, A. T. Diplock, pp. 1–9, 1985).
Vitamins and Amino Acids, B. Borenstein, CRC Handbook of Food Additives, 2nd ed., Chapter 2, pp. 85, 87, 91–93, 102–104, 107–109, CRC Press, Inc. (1972).
Fat-Soluble Vitamins, Introductory Nutrition, H. A. Guthrie, pp. 188–190, C. V. Mosby Co. (1971).

*Primary Examiner*—Werren B. Lone
*Attorney, Agent, or Firm*—Rose Ann Dabek; J. C. Rasser

[57] ABSTRACT

A process for purifying vitamin A consisting of heating a vitamin A preparation in an inert atmosphere, at a temperature below 170° C. and a pressure of less than 4 mm of mercury, said heating taking place in a vessel shielded from light is disclosed. The vitamin A obtained from this process is mixed with from 0.5:1 to 2:1 parts of tocopherol to vitamin A. The vitamin A and tocopherol mixture can be encapsulated in acacia gum, starch, pectins or other suitable materials. Other antioxidants can be added.

19 Claims, No Drawings

STABLE VITAMIN A

TECHNICAL FIELD

The field of this invention is a purified and stabilized vitamin A or vitamin A derivative which is substantially free of off flavor and is odorless.

BACKGROUND OF THE INVENTION

Vitamin A is commercially prepared by extraction from fish liver oils or by chemical synthesis from the reaction of beta ionone and a propargyl halide. Other syntheses include starting with beta ionone, converting it to beta iononyl, and reacting it with 3-formylcrotonyl acetate to make retinol acetate. Alternatively, beta ionone can be convened to the corresponding aldehyde and through a Grignard reaction with 3 methyl-2-pentene-4-yn-1-ol and a partial hydrogenation and rearrangement converts it to retinol acetate. Retinol acetate is converted to retinol palmitate through a transesterification reaction with methyl palmitate. Both retinol acetate and retinol palmitate are commonly used for supplementation.

The most stable and more bioavailable form of Vitamin A is the trans isomer. The cis isomeric forms, i.e., 13-cis retinol, 9-cis retinol, and 9, 13-di-cis retinol materials are less stable. Cis isomers are formed during production and they oxidize more readily than the trans isomers.

Commercial vitamin A contains a number of impurities which are present either due to oxidation or as left over solvents or by products of the synthesis of vitamin A. One of the key reactants and/or oxidation products of vitamin A is beta ionone. The percentage of beta ionone as well as the level of cis isomers of vitamin A can be used to determine vitamin A quality.

Even when vitamin A palmitate or acetate is prepared and purified, it readily oxidizes creating beta-ionone and other oxidation products. Spray dried vitamin A that is, vitamin A which is spray dried or partially encapsulated with pectin, starches, gum, or other suitable material, is more stable to oxidation, but it also can contain from 10-30% cis isomers vitamin A and solvents remaining from the synthesis or the transesterification reaction. Even this form of vitamin A can oxidize over time.

Beta ionone which is a key impurity in vitamin A has a cedar wood or raspberry aroma and is used in perfumes. It has a very low threshold level. This is just one of many odors associated with vitamin A oxidation products. Aldehydes and ketones are also formed, particularly hexanal, 5-nonen-2-one, 2-decenal, and octanal. Hydrocarbons such as hexane, cyclopentane, ethyl cyclohexane and nonane can also be present. All of these materials have unpleasant odors and flavors.

Accordingly, it is desirable to have a vitamin A which is substantially free of oxidation products, solvents, and has less than 5% of the cis isomer. Such a vitamin A has been found to be tasteless and odorless. It would also be desirable to stabilize this material against oxidation.

It has now been found that vitamin A can be purified to remove essentially all of the volatile materials boiling below 50° C., and, stabilized to prevent further oxidation. It is therefore an object of this invention to provide a tasteless, odorless, storage-stable vitamin A. It is also an object of this invention to make a vitamin A which contains β-ionone at levels below its threshold value.

These and other objects of the invention will be evident from the description following.

SUMMARY OF THE INVENTION

A process for purifying vitamin A consisting of heating a vitamin A preparation in an inert atmosphere, at a temperature below 170° C. and a pressure of less than 4 mm of mercury, said heating taking place in a vessel shielded from light is disclosed. The vitamin A obtained from this process is mixed with from 0.5:1 to 2:1 parts of tocopherol to vitamin A. The vitamin A and tocopherol mixture can be encapsulated in acacia gum, starch, pectins, lipid hardstocks, ethyl cellulose or other suitable materials. Other antioxidants can be added.

DETAILED DESCRIPTION OF THE INVENTION

All percentages used herein are by weight unless otherwise indicated.

As used herein, the term "comprising" encompasses the more narrow terms "consisting essentially of" and "consisting of".

As used herein, the term "Vitamin A" includes retinol and the alkyl esters of vitamin A. The alkyl ester group can have from 2 to 22 carbon atoms and can be saturated, branched or straight chain. Unsaturated alkyl groups can also be used, but they are less preferred because of their tendency to oxidize. Dehydroretinol (Vitamin $A_2$) and vitamin A aldehyde or retinene are also included in the term "vitamin A".

THE PROCESS

Vitamin A is placed in a vessel which is shielded from light sources. A metal vessel or glass vessel which has been painted black or coated with a black or non-light transmitting coating is acceptable.

Vitamin A is degassed by any conventional method. It is important to remove any dissolved oxygen from the vitamin A since oxygen can cause further oxidation or degradation of vitamin A in the initial heating steps used to purify the material. Preferably vitamin A is subjected to a vacuum of less than 5 mm of mercury to degas the sample. Usually the sample is degassed at less than 0.5 mm Hg.

An inert gas sparge is then introduced into the sample. Preferably nitrogen is used as the sparging agent. However, non-oxidizing gases such as carbon dioxide, helium, argon or neon can also be used.

The sample is then heated to a temperature below 170° C., preferably in the range of from about 95° C. to about 150° C., and most preferably from about 130° C. to about 150° C. The rate of heating is not critical. Generally the vitamin A is heated from room temperature to 150° C. in 2-3 minutes.

The sample is heated and sparged with inert gas under reduced pressure, less than 5 mm of mercury, preferably less than 1, and most preferably in the range of 0.3 mm to 0.6 mm of mercury. The preferred heating conditions are from about 130° C. to about 150° C., with a pressure in the range of about 0.5 mm of mercury. The sparging gas is provided to the vessel at a flow rate of 0.5 to 14 cc/min/g vitamin A. Under these temperature and pressure conditions most of the oxidation products and hydrocarbons volatilize and are removed with the nitrogen or inert gas sparging.

Since beta ionone is one of the key impurities and since its boiling point is 126° C. at 12 mm of mercury, it is used to measure the progress of the purification of the vitamin A. Many of the impurities boil or vaporize with or before beta ionone under these conditions Thus, the absence of beta ionone can be used as an indicator that many of the hydrocarbons and lower molecular weight oxidation products have been removed. The presence of beta ionone can be detected using a gas chromatograph to analyze the volatiles obtained by heating the sample to 50° C. Other analysis techniques can also be used.

Conventional oil deodorization or stripping equipment can be used. Then film evaporators, molecular still and deodorization units (batch or continuous) are acceptable.

It generally takes up to 120 minutes to remove the impurities. The exact time depends on sample size and the vessel configuration and the efficiency of the system. For a rotary evaporator from 15 minutes to 120 minutes is required. For a wiped film evaporator the removal of impurities is accomplished in less than 10 minutes and usually on the order of 30 seconds to 5 minutes.

The purified vitamin A is mixed with tocopherol, and degassed again if necessary. Any tocopherol isomer can be used. The most preferred isomer is the alpha isomer which is also vitamin E. Tocopherol acts as an anti-oxidant and also reduces the amount of oxygen contacting the vitamin A. Tocopherol oxidizes less readily than vitamin A, and thus, is effective in stabilizing purified vitamin A. Generally from 0.5:1 to 2:1 parts of tocopherol to vitamin A are used. The tocopherol can be added to the vitamin A prior to the purification step also. Preferably the ratio of tocopherol to vitamin A is 0.75:1 to 1:1.

The vitamin A prepared by the process herein is characterized by the following composition:

| COMPONENT | PERCENT BY WEIGHT |
| --- | --- |
| vitamin A, trans isomer | 33 to 66 |
| tocopherol | 33 to 66 |
| beta-ionone | 0 to 0.33 |
| cis-isomers of vitamin A | 0 to 0.33 |

It is substantially free of beta-ionone and solvents. By "substantially free" is meant that the levels of these materials in the vitamin A are less than 5% by weight of the vitamin A content. The level of $\beta$-ionone and other hydrocarbon impurities are measured by a gas chromatographic method. These materials are volatile at 50° C. and their concentration in the headspace of the sample tube is proportional to their concentration in the vitamin A. Measuring the total decrease in $\beta$-ionone content in the volatiles conrims the low levels of impurities remaining in the vitamin A.

The vitamin A and tocopherol mixture can be in the form of a liquid oil, spray dried or encapsulated with gums, starches, pectin, lipid hardstocks, ethyl cellulose or other suitable materials. Preferably, dextrin and gum acacia are used for the encapsulation. Any conventional encapsulation technique can be used to prepare such products. The vitamin A and tocopherol can also be admixed with other food ingredients.

The product prepared by this process is stable for up to three months against oxidation, and is essentially tasteless and odorless. To prolong the stability of purified vitamin A it should be stored in an oxygen free atmosphere and protected from light. Opaque packaging or an amber bottle can be used to protect it during storage.

Other antioxidants such as BHA, BHT and ascorbyl palmitate can be added to the compositions. In a preferred embodiment materials that suppress oxygen permeability into the vitaminA/tocopherol mixture are added. For example, stearyl alcohol can be used for this purpose. The stearyl alcohol forms a crystal lattice which will protect the vitamin A by providing a protective layer.

EXAMPLE I

A 500 ml cylindrical vessel which has been shielded from light and equipped to work with a rotary evaporator is charged with a 41.2 gm sample of unstabilized high potency vitamin A palmitate. The vessel is equipped with a dip tube which can be used to sparge the vessel with nitrogen. The volatiles are collected onto a cold finger condenser. The sample is first placed under vacuum at 0.1 mm of mercury to degas the sample. The nitrogen sparge is then introduced at a flow rate of ~8 cc/min./g sample. The sample is quickly heated to a temperature of 150° C. by immersing the vessel in an oil bath maintained at 150° C. The introduction of the nitrogen sparge causes the vacuum to rise to 0.5 mm of mercury. The product is heated for 120 minutes under these conditions.

The vitamin A is then cooled to room temperature, the vessel opened, and alpha-tocopherol mixed with it. The mixture is then degassed under 0.1–0.5 mmHg. then saturated with nitrogen. The ratio of alpha tocopherol to vitamin A palmitate is 1:1 by weight.

This material is then mixed with potato starch to a concentration of 5% vitamin A palmitate and sprinkled on to a potato chip. When 32 panelists were asked to evaluate the product for off flavor, acceptability, saltiness and potato flavor, 80% of the panelists saw no difference between the control sample without vitamin A addition and the product containing the vitamin A and E mixture; 17% of the panelists found less off flavor in the vitamin A and E product. The product contained 210 ppm of vitamin A and 210 ppm of tocopherol.

A high quality commercial vitamin A powder which had not been purified by the process described herein was tested at 150 ppm level on potato chips. In this panel only 48% of the panelists saw no difference and 36% of the panelists indicated that the vitamin A sample had more off flavor.

EXAMPLE II

Four different conditions were used to purify a commercial vitamin A sample having 1.8 million IUs (International Units). The general treatment was as in Example I. Before the sample was purified the volatiles at 50° C. were analyzed by gas chromatography using the method described below. This sample is designated as the Control.

The purified vitamin A was analyzed by the same method. The results are provided in the following table. As is evident, the total amount of volatiles decreased by about 60% with all of the treatments. Importantly, the amount of $\beta$-ionone was decreased significantly in the samples.

| Volatile Measurements on Vitamin A Liquids | | | | | |
| --- | --- | --- | --- | --- | --- |
|  | Control | 1 | 2 | 3 | 4 |
| Temperature | — | 95° C. | 150° C. | 170° C. | 150° C. |
| Pressure (mmHg) | — | 2–3 mmHg | 3–4 mmHg | 3–4 mmHg | 0.5 mmHg |
| Time (min.) | — | 120 | 120 | 120 | 120 |
| Sample wt. grams | 0.102 | 0.126 | 0.145 | 0.130 | 0.136 |
| Total Peak Area | 786508 | 160217 | 120578 | 256278 | 801 |
| β-ionone Count/g. sample | 16373 | 3201 | 2202 | 4959 | 59 |

Analytical Procedure

Gas Chromatographic Monitoring of Volatile Components

Sampling System

The sampling system consists of a Tekmar LSC 2000 Purge and Trap unit fitted with a 5 ml needle sparge tube. The sparge tubes are impeccably cleaned and baked at 140° C. prior to use. The Purge and Trap unit is prepared for use by cycling it through multiple blank runs while baking the trap at a temperature of 225° C. for 8 minutes. This continues until the trap is essentially clean of any background contaminants.

Approximately 0.150 grams of test material is weighed directly into a cool sparge tube and immediately placed on the Tekmar unit. The sample is heated to 50° C. and purged with nitrogen at volumetric flow rate of 6–20 cc/minute for 4 minutes. Volatiles are collected onto a trap containing Tenax GC adsorbent. When complete, the trap is preheated to 100° C. for 2 minute. The trap is then back flushed at a desorb temperature of 180° C. for 4 minutes. Transfer lines and switching valve are maintained at 200° C. The sample mounting block is maintained at 100° C.

The desorbed volatiles are flushed into a Hewlett Packard 5890 gas chromatograph equipped with a Hewlett Packard 3396 electronic integrator. The detector is a flame ionization type. The fused silica capillary column is 50 meters long by 0.25 mm internal diameter. The capillary column is a DB-1 type.

The gas chromatograph uses a split injection flow. Initial oven temperature is 40° C. The chromatograph is programmed to automatically change the temperature of the oven at the rate of 10° C./minute to a final oven temperature of 350° C. Initial oven hold time is 5 minutes. The injector temperature is 200° C. and the detector temperature is 350° C. The split ratio is set at 10 to 50 ml/minute.

The integrator is set at manufacturer's recommendations so the peak integrations are optimized.

The recorder is a linear recorder which did not change the attenuation according to peak height.

Food Uses

The shelf stable purified vitamin A can be used in any food product. It can be added to oils, breads, baked goods, confections, snacks, beverages and other oil containing foods. It can also be used in cosmetics and in vitamin supplements. It is particularly useful in liquid supplements where taste and odor are a problem.

What is claimed is:

1. A shelf stable, purified vitamin A preparation which is substantially free of beta-ionone and solvents, and wherein less than 5% of the vitamin A is a cis-isomer comprising a mixture of tocopherol and vitamin A, the ratio of tocopherol to vitamin A being from 0.5:1 to 2:1.

2. A vitamin A according to claim 1 wherein the ratio of tocopherol to vitamin A is from 0.75:1 to 1:1.

3. A vitamin A according to claim 2 wherein the vitamin A is an alkyl ester of retinol.

4. A vitamin A according to claim 3 wherein the vitamin A is retinol acetate or retinol palmitate.

5. A vitamin A according to claim 2 wherein the tocopherol is alpha tocopherol.

6. A vitamin A according to claim 5 which contains less than 3% beta-ionone and less than 2% cis-isomers of vitamin A based on the weight of vitamin A.

7. A vitamin A according to claim 1 which contains less than 3% beta-ionone and less than 2% cis-isomers of vitamin A based on the weight of vitamin A.

8. A process for removing off-flavor and odors from vitamin A comprising:
   (a) degassing a sample of vitamin A;
   (b) heating degassed vitamin A in the absence of light at a pressure of less than 4 mm Hg and a temperature of less than 170° C. with an inert gas sparge until substantially of all the beta-ionone and solvents are removed;
   (c) mixing the vitamin A with from about 0.5 to 2 parts of tocopherol/part of vitamin A.

9. A process according to claim 8 wherein the vitamin A is mixed with the tocopherol before the heating step.

10. A process according to claim 8 wherein the vitamin A is heated at a temperature of from about 130° C. to about 150° C. at a pressure of from 0.3 to about 0.6 mm Hg.

11. A process according to claim 9 wherein the vitamin A is heated at a temperature of from 130° C. to 150° C. at a pressure of about 0.3 to about 0.6 mm Hg.

12. A process according to claim 11 wherein the sparging gas is nitrogen.

13. A process according to claim 8 wherein the ratio of tocopherol to vitamin A is from 0.75:1 to 1:1.

14. A process according to claim 13 wherein the vitamin A is an alkyl ester of retinol.

15. A process according to claim 14 wherein the vitamin A is retinol acetate or retinol palmitate.

16. A process according to claim 13 wherein the tocopherol is alpha tocopherol.

17. A process according to claim 15 wherein the vitamin A contains less than beta-ionone and less than 2% cis-isomers of vitamin A based on the weight of vitamin A.

18. A process according to claim 11 which contains less than 3% beta-ionone and less than 2% cis-isomers of vitamin A based on the weight of vitamin A.

19. A food product comprising the composition of claim 1.

* * * * *